United States Patent [19]

Myint

[11] 4,313,337

[45] Feb. 2, 1982

[54] APPARATUS FOR EVALUATING THE IMPACT RESISTANCE OF SYNTHETIC RESINOUS PRODUCTS

[75] Inventor: U. Hla Myint, Kowloon, Hong Kong

[73] Assignee: The Dow Chemical Company, Midland, Mich.

[21] Appl. No.: 130,756

[22] Filed: Mar. 17, 1980

[51] Int. Cl.³ ............................................. G01N 3/34
[52] U.S. Cl. ....................................................... 73/12
[58] Field of Search .................................. 73/12, 810

[56] References Cited

U.S. PATENT DOCUMENTS

| | | | |
|---|---|---|---|
| 2,892,342 | 6/1959 | Goss et al. | 73/12 |
| 4,116,041 | 9/1978 | Tholen et al. | 73/12 |
| 4,168,620 | 9/1979 | Schrader | 73/12 |

FOREIGN PATENT DOCUMENTS 836023  6/1960  United Kingdom .................... 73/12

*Primary Examiner*—James J. Gill
*Attorney, Agent, or Firm*—D. R. Howard

[57] ABSTRACT

An improved apparatus for evaluating the practical impact resistance of synthetic resinous products employing a pneumatically operated apparatus for repeatedly raising and dropping an impact hammer against an impact member which is oriented generally normal to a synthetic resinous product sample which, in turn, is maintained in a generally fixed position with respect to the impact member so that the impact energy which results when the impact hammer strikes the impact member impacts with the sample at generally the same point with each repetition, said impact energy being of a magnitude such that there is substantially no rebounding of the impact member from the synthetic resinous product sample.

8 Claims, 7 Drawing Figures

APPARATUS FOR EVALUATING THE IMPACT RESISTANCE OF SYNTHETIC RESINOUS PRODUCTS

BACKGROUND OF THE INVENTION

In the preparation of synthetic resinous products, it is often desirable to have an apparatus for evaluating the impact resistance of a synthetic resinous product which corresponds closely to practical toughness of the synthetic resinous product in end-use applications.

Experience has indicated the advisability of modifying or creating new testing apparatus to ensure reproducible, meaningful results. Previous evaluation methods have ranged from error-prone, subjective tests, such as striking vacuum cleaner suction heads (formed from synthetic resinous materials) against rigid walls and throwing toys (formed from synthetic resinous materials) down a flight of stairs, to the more objective tests, such as the notched Izod impact test wherein a large swinging pendulum strikes a test specimen into which notches have been machined, the measure of impact resistance being the distance which the pendulum travels after breaking the test specimen.

U.S. Pat. No. 2,892,342 discloses a testing apparatus which is used to determine the fatigue and impact strength of plastic materials whereby a weighted hemispherical shape is repeatedly raised and dropped against a test piece until sample failure occurs.

Experience has demonstrated that the practical impact performance of formed synthetic resinous products does not necessarily depend upon the Izod impact test value for the particular resin. Rather, the practical impact performance depends upon a combination of a number of other properties such as tensile rupture, percent elongation, percent gel, or swell index of the rubber phase.

It would be desirable if there were available an improved apparatus for the testing of synthetic resinous products.

It would also be desirable if such an apparatus yielded reproducible results.

It would be desirable if the impact portion of the apparatus had a reduced tendency to rebound from the surface of the test piece upon impact.

It would further be desirable if such an apparatus were inexpensive.

SUMMARY OF THE INVENTION

These features and other advantages in accordance with the present invention are achieved in an improved impact testing apparatus of the type used for the evaluation of synthetic resinous products or test pieces in which a support means serves as a base in cooperative combination with a peripherally supporting sample support means, a slidably supported sample impacting means which is oriented generally normal to the sample support means, and a means for varying the height to which the sample impacting means is raised and dropped thereby imparting an impact energy to an impact region of a test piece, said impact region being a generally central unsupported surface portion of the test piece, and repeatedly imparting the impact energy until failure of the test piece occurs, wherein the improvement comprises:

a sample impacting means having two pieces, an impact member and an impact hammer, both of which are slidably supported by the support means, the impact member having a first end which rests against at least a surface portion of the impact region of the test piece, and a second end which is remote from the first end, the impact force being imparted to the impact region when the impact hammer strikes the second end of the impact member and being of a magnitude such that there is substantially no rebounding of the first end of the impact member away from the impact region after the impact energy is imparted.

Further features and advantages of the present invention will become more apparent from the following specification taken in connection with the drawings wherein.

DETAILED DESCRIPTION OF THE INVENTION

Figure 1:
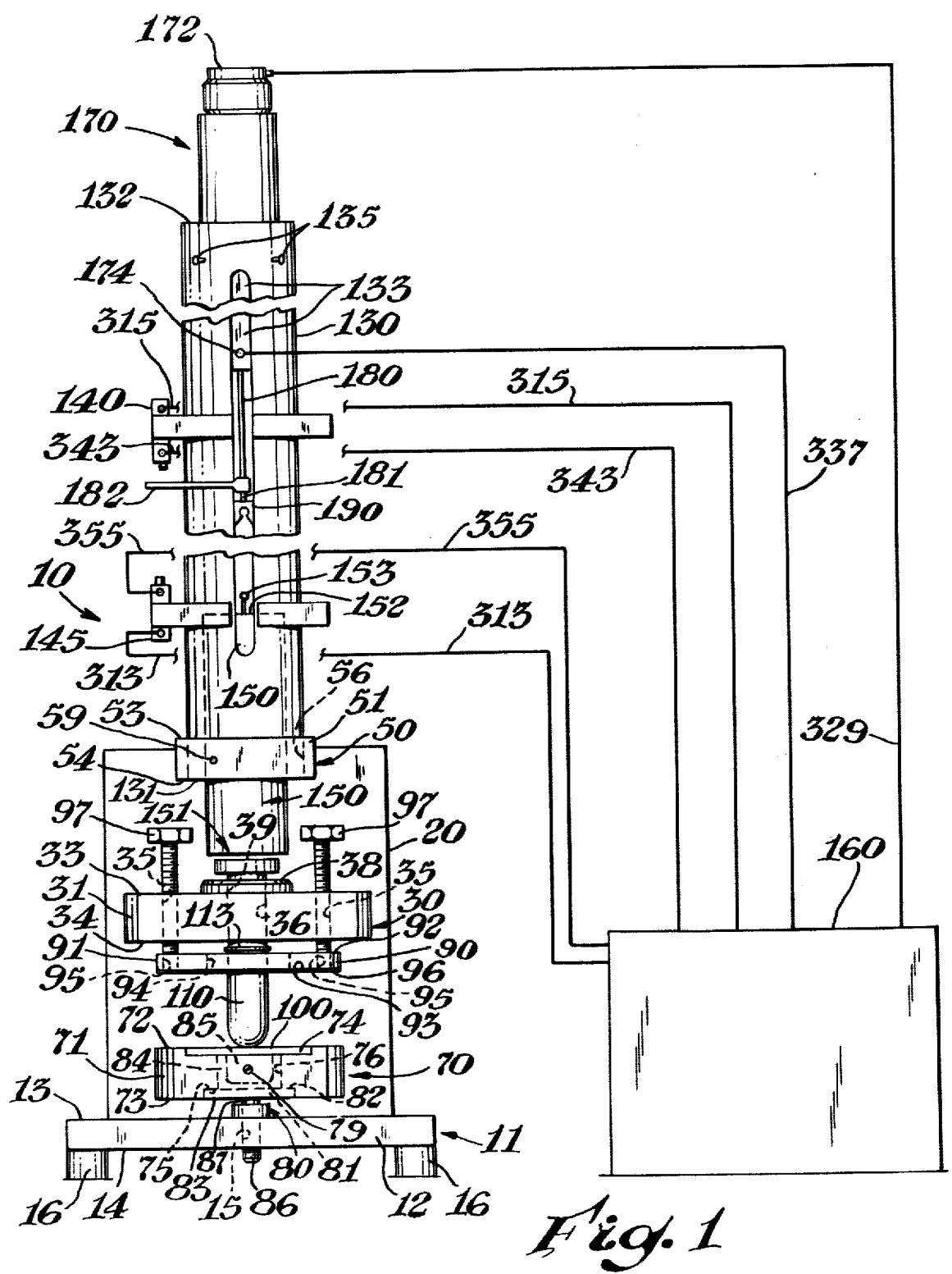
FIGS. 1 and 2 are schematic illustrations of an impact testing apparatus in accordance with the present invention.
Figure 2:
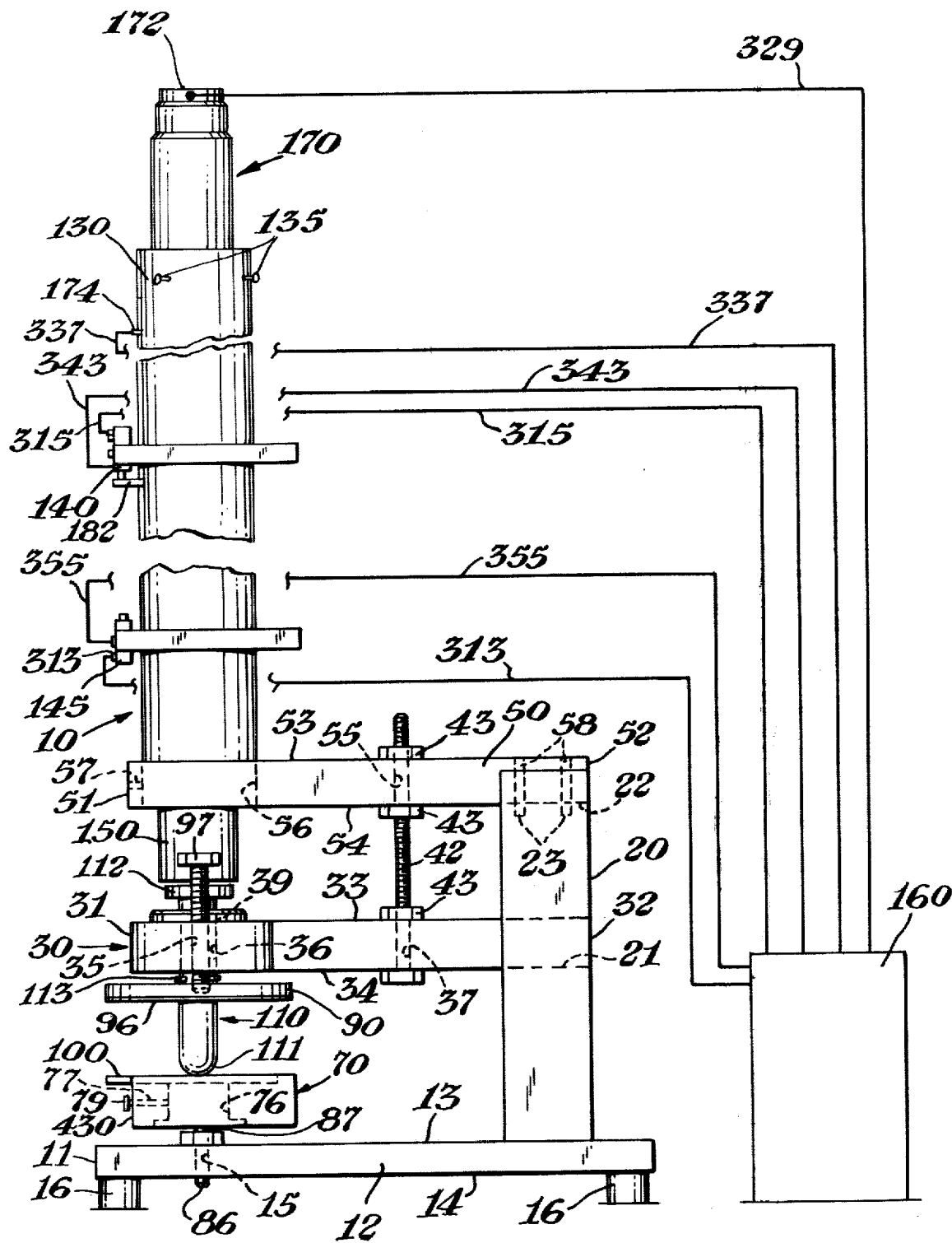

In FIGS. 1 and 2, there is schematically depicted an apparatus, in accordance with the present invention, generally designated by the reference numeral 10. The apparatus 10 comprises a base 11, an impact member 110, a double-acting pneumatic cylinder 170, a hollow right circular cylinder 130, an impact hammer 150 and a control assembly 160. The base 11 comprises a base plate 12, a vertical support member 20, an impact member support arm 30, a pneumatic cylinder support arm 50, a sample support means 70 and a synthetic resinous product sample restraining means 90. The base plate 12 has a first planar surface 13, an opposing second planar surface 14 and an internally screw-threaded aperture 15. Affixed to the planar surface 14 are four legs 16.

The vertical support member 20 is affixed to the first planar surface 13 of the base plate 12. The vertical support member 20 has defined therein a generally rectangular aperture 21 and a generally rectangular recess 22, said recess having four internally screw-threaded recesses 23, the number of recesses 23 not being selected by way of limitation.

The impact member support arm 30 has a first end 31, a second end 32, a first planar surface 33, an opposing second planar surface 34, two internally screw-threaded apertures 35, a smooth-surfaced aperture 36, an aperture 37 which is optionally internally screw-threaded, and an axially extending buffer boss 38. The smooth-surfaced aperture 36 is preferably circular. The first end 31 is generally wide enough to define the two internally screw-threaded apertures 35, the smooth-surfaced aperture 36, and the axially extending buffer boss 38 which is affixed to the first planar surface 33 of the impact member support arm 30. The axially extending buffer boss 38 defines an aperture 39 which is advantageously of the same shape and dimension as the smooth-surfaced aperture 36 within the impact member support arm 30.

The axially extending buffer boss 38 is positioned so that the axis of the aperture 39 is coaxial with the axis of the smooth-surfaced aperture 36. The second end 32 preferably has the same generally rectangular shape and dimension as the aperture 21 within the vertical support member 20. The impact member support arm 30 is connected to the vertical support member 20. Any means may be used to secure the impact member support arm 30 to the vertical support member 20 so long as the impact member support arm 30 is maintained in a generally fixed position.

The pneumatic cylinder support arm 50 has a first end 51, a second end 52, a first planar surface 53, an opposing second planar surface 54, an aperture 55 which is optionally internally screw-threaded, a smooth-surfaced aperture 56, an internally screw-threaded aperture 57 which is generally normal to, and which intersects with, the smooth-surfaced aperture 56, and four internally screw-threaded apertures 58, the number of apertures 58 not being selected by way of limitation so long as the number of apertures 58 within the pneumatic cylinder support arm 50 equals the number of recesses 23 within the vertical support member 20. The pneumatic cylinder support arm 50 is affixed to the vertical support member 20 by inserting the second end 52 of the pneumatic cylinder support arm 50 into the generally rectangular recess 22 within the vertical support member 20 in such a manner that the apertures 58 within the pneumatic cylinder support arm 50 are generally coaxial with the recesses 23 within the vertical support member 20 and by threadably engaging a screw (not shown) with one or more of the four parallel internally screw-threaded apertures 58 in such a manner that the screw also threadably engages the screw-threaded recesses 23. When the base 12, the vertical support member 20, the impact member support arm 30, and the pneumatic cylinder support arm 50 are assembled in this configuration, aperture 55 within the pneumatic cylinder support arm 50 is generally coaxial with the aperture 37 within the impact member support arm 30 and the smooth-surfaced aperture 56 within the pneumatic cylinder support arm 50 is generally coaxial with aperture 36 within the impact member support arm 30 and the internally screw-threaded aperture 15 within the base plate 12. A cap screw 42 passes through the aperture 37 within the impact member support arm 30 and the aperture 55 within the pneumatic cylinder support arm 50 and is secured in place by three nuts 43. The nuts 43 are optionally of the locking variety.

The sample support means 70 comprises a peripherally supporting reversible sample receiving means (hereinafter sample receiving means) 71 and a ring pedestal 80. The sample receiving means 71 has a first planar surface 72, an opposing second planar surface 73, said sample receiving means 71 defining a recess 74 in the first planar surface 72, a recess 75 in the opposing second planar surface 73, a smooth-surfaced aperture 76 which is axially located, and an internally screw-threaded aperture 77 which is generally normal to, and which intersects with, the smooth-surfaced aperture 76, and a set screw 79 which is threadably engaged with the internally screw-threaded aperture 77. The sample receiving means 71 is in the shape of a partial cylinder with a flat surface 430 formed thereon, said flat surface 430 being parallel to the axis of generation of the cylinder surface. The recess 74 which is defined in the first end 72 of the sample receiving means 71 is advantageously of a greater diameter but a lesser depth than the recess 75 which is defined in the second end 73 of the sample receiving means 71. The smooth-surfaced aperture 76 is advantageously cylindrical and is a slidable fit over the ring pedestal 80. The internally screw-threaded aperture 77 is defined by the flat surface 430 and is positioned so that its axis intersects with a radially outward facing groove (not shown) on the ring pedestal 80. The ring pedestal 80 comprises a generally discoidally shaped base 81, said base 81 having a first planar surface 82 and an opposing second planar surface 83, a generally cylindrical boss 84 coaxially mounted on the first surface 82, said boss 84 generally defining a coaxial cavity 85, and an externally screw-threaded stud 86 coaxially mounted on the second surface 83, said stud 86 having a region 87, proximate to the second surface 83, which is not externally screw-threaded. The boss 84 preferably has a discontinuous circular recess or radially outward facing groove (not shown) said recess being positioned so that it may receive the set screw 79 which is threadably engaged with the internally screw-threaded aperture 77 within the sample receiving means 71.

The sample support means 70 is attached to the base 12 by threadably engaging the externally screw-threaded stud 86 with the internally screw-threaded aperture 15, thus causing the cavity 85, the smooth-surfaced aperture 76, the aperture 15 and the aperture 36 to be generally coaxial.

A synthetic resinous product sample or test specimen 100 is placed against that surface of the sample receiving means 71 which is remote from the base plate 12. The synthetic resinous product sample 100 is discoidally shaped having a thickness generally equal to the depth of either the recess 74. Optionally a synthetic resinous product sample has generally the same dimensions as the recess 75. Alternately, a sample may be selected from a portion of a finished synthetic resinous product which has at least one external surface.

The synthetic resinous product sample restraining means or sample restraint means 90 comprises a generally annular plate 91, a slip-resistant material, or material having a high coefficient of friction, 96, two cap screws 97 and two peripherally located internally screw-threaded apertures 95 which are generally diametrically opposed. The generally annular plate 91 is has a first planar surface 92, an opposing second planar surface 93, and a generally circular axially located aperture 94, having a diameter which is greater than that of the coaxial cavity 85 of the ring pedestal 80 but less than that of recess 74 or recess 75 of the sample receiving means 71. The cap screws 97 are threadably engaged with the internally screw-threaded apertures 35 within the impact member support arm 30 and threadably engaged in the internally screw-threaded apertures 95. Optionally, the internally screw-threaded apertures 95 are cavities and while two apertures or cavities are preferred that quantity is not selected by way of limitation. The slip-resistant material 96 is generally ring-shaped with an opening generally equal in size and shape to that of the circular axially located aperture 94 of the synthetic resinous product sample restraining means 90 and is affixed to the second surface 93 of the synthetic resinous product sample restraining means 90. The synthetic resinous product sample restraining means 90 may be raised or lowered, as desired, by turning the cap screws 97 in the appropriate direction.

An impact member 110 is slidably supported within the smooth-surfaced aperture 36 of the impact member support arm 30 and oriented so that the longitudinal axis of the impact member 110 is generally normal to the synthetic resinous product sample 100 and so that an end of the impact member 110 rests against that external surface of the synthetic resinous product sample 100 which is remote from the base plate 12 of the apparatus 10. The impact member 110 comprises a generally solid rotationally symmetrical body having a first end 111, a second end 112, and a radially outward facing annular groove (not shown) which is located on the body of the impact member 110. The first end 111 generally defines a hemispherical shape. The second end 112 generally defines a radially outward projecting flange. The first end 111 of the impact member 110 is that end which rests against the surface of the synthetic resinous product sample 100 which is remote from the base plate 12. The slidable motion of the impact member 110 is limited by inserting a spring-retaining ring 113 into the outward facing annular groove (not shown) which is located on the body of the impact member 110.

A hollow right circular cylinder 130 having one end affixed to the pneumatic cylinder support arm 50 is oriented so that its longitudinal axis is generally coaxial with the axis of generation of the impact member 110. The hollow right circular cylinder 130 has a first end 131, a second end 132, a slot 133 and three apertures (not shown) said quantity of apertures not being selected by way of limitation. The slot 133 parallels the longitudinal axis of the cylinder 130 and approaches, but does not reach, either end 131 or end 132. The three internally screw-threaded apertures are generally equally spaced about the circumference of the hollow right circular cylinder 130 proximate to the second end 132. The axis of each internally screw-threaded aperture is radially outwardly projecting. The hollow right circular cylinder 130 is affixed to the pneumatic cylinder support arm 50 by inserting the first end 131 into the aperture 56 until the first end 131 is tangential to the second planar surface 54 and by tightening a set screw 59 which is threadably engaged with the aperture 57 within the first end 51 of the pneumatic cylinder support arm 50 until the hollow right circular cylinder 130 is generally held immobile.

An impact hammer 150 is slidably supported within the hollow right circular cylinder 130 and oriented so that its longitudinal axis is generally coaxial with the longitudinal axis of the hollow right circular cylinder 130. The impact hammer 150 comprises a solid right cylindrical body having a first end 151 and a second end 152. A lift mechanism engaging means, or headed projection, 153 is mounted on the second end 152 of the impact hammer 150 generally coaxial with the axis of generation of the impact hammer 150. The headed projection 153 comprises a shaft portion and a head portion, the head portion being remote from the second end 152 of the impact hammer 150 and having outward facing camming surfaces which are outwardly divergent toward the body of the impact hammer 150. The impact hammer 150 is slidably supported within the hollow right circular cylinder 130 so that the first end 151 is adjacent to the second end 112 of the impact member 110.

A double-acting pneumatic cylinder 170 is provided as a means of imparting a reciprocal motion to a means for causing the impact hammer 150 to move alternately toward and away from the second end 112 of the impact member 110. The double-acting pneumatic cylinder 170 has a first end (not shown) and a second end 172. The double-acting pneumatic cylinder 170 has incorporated therein a piston (not shown) which has affixed thereto a piston rod 180. The piston rod 180 has a first end (not shown) attached to the piston (not shown) and a second end 181. The second end 181 terminates in a means 190 for alternately grasping and releasing the headed projection 153 of the impact hammer 150. A valve actuating arm 182 is affixed to the piston rod 180 proximate to the means 190, said valve actuating arm 182 being generally normal to the rod 180. The double-acting pneumatic cylinder 170 is partially contained within and is affixed to the hollow right circular cylinder 130, said affixation being by means of three set screws 135 which are threadably engaged with the three internally screw-threaded apertures (not shown) which are located proximate to the second end 132 of the hollow right circular cylinder 130. When combined in this manner the second end 172 of the double-acting pneumatic cylinder 170 projects from the second end 132 of the hollow right circular cylinder 130 and the valve-actuating arm 182 protrudes from and is slidably disposed with the slot 133 of the hollow right circular cylinder 130. Attached to the hollow right circular cylinder 130 is a first limit valve 140 and a second limit valve 145. The first limit valve 140 is oriented in such a manner that it will be actuated by the valve-actuating arm 182 when the valve-actuating arm 182 moves generally toward the second end 132 of the hollow right circular cylinder 130. The second limit valve 145 is oriented in such a manner that it will be actuated by the valve-actuating arm 182 when the valve-actuating arm 182 moves generally away from the second end 132 of the hollow cylinder 130. The first limit valve 140 is positioned so that the actuation of the first limit valve 140 by the valve-actuating arm 182 is generally concurrent with the grasping of the headed projection 153 of the impact hammer 150 by the means 190. The second limit valve 145 is positioned so that the actuation of the second limit valve 145 by the valve-actuating arm 182 is generally concurrent with the releasing of the headed projection 153 of the impact hammer 150 by the means 190. The second limit valve 145 is further positioned so that when the headed projection 153 of the impact hammer 150 is released by the means 190, the first end 151 of the impact hammer 150 is at a preselected distance removed from the second end 112 of the impact member 110, said distance being that which will yield a desired impact energy when the distance is multiplied by the weight of the impact hammer 150. Following release of the headed projection 153, the impact hammer 150 will move slidably toward the impact member 110. The impact energy is imparted concurrent with the impacting of the first end 151 of the impact hammer 150 with the second end 112 of the impact member 110. A control assembly 160, not shown in detail, serves to supply a motive fluid under pressure, such as lubricated, compressed air, and to count the number of times the impact hammer 150 impacts with the second end 112 of the impact member 110.

Figure 3:
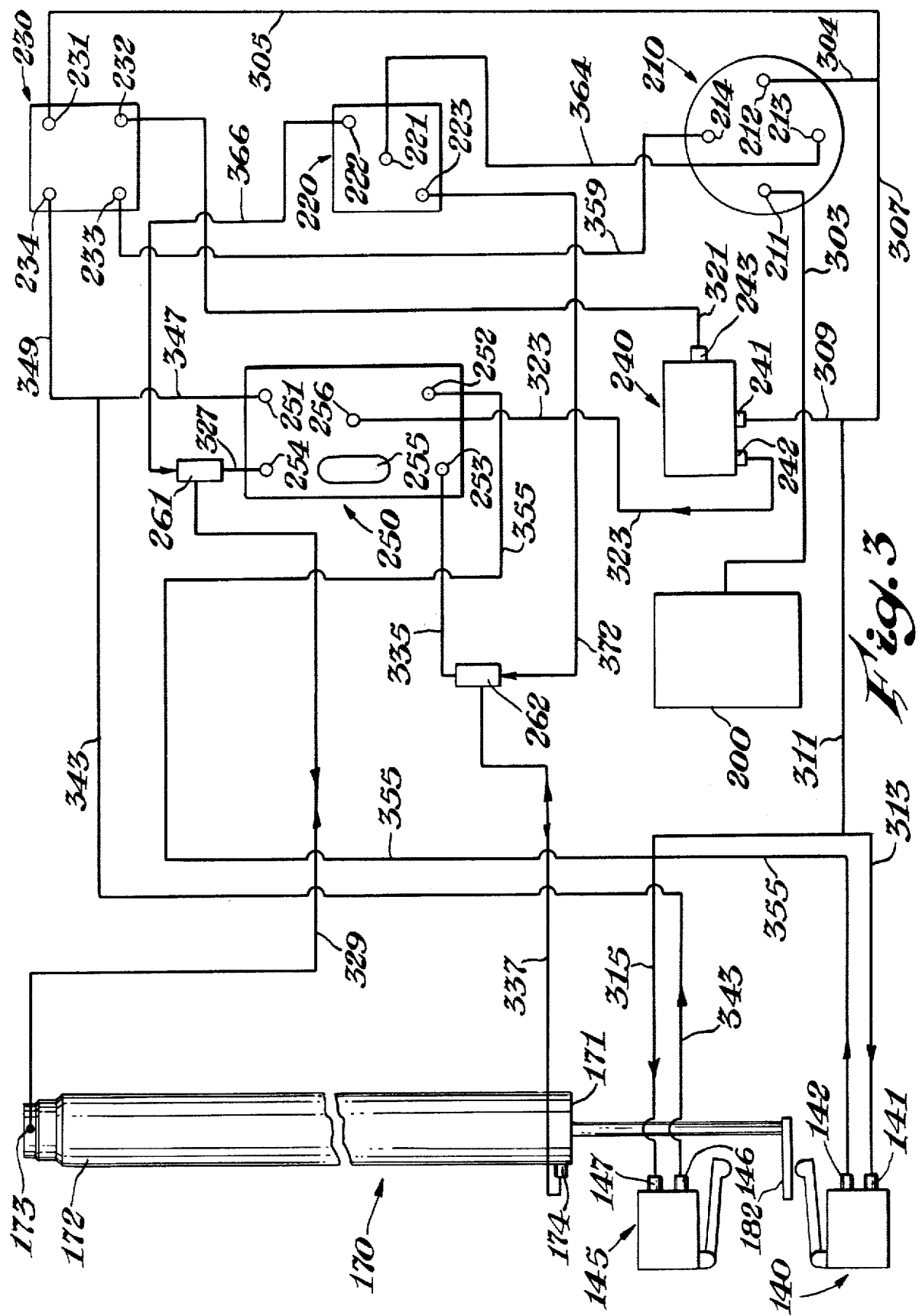
FIG. 3 is a schematic diagram of a pneumatic system which may be used in accordance with the present invention.

In FIG. 3, there is schematically depicted a control assembly generally designated by the reference numeral 160.

The control assembly 160 comprises the first limit valve 140, the second limit valve 145, a source of motive fluid under pressure, such as lubricated compressed air, 200, a valving means which comprises control devices 210, 220, 230, 240, 250, 261 and 262 and connecting lines and valves which serve to interconnect the control devices.

The control device 210 is a multiport valve, having ports 211, 212, 213 and 214, which permits selective interconnection of port 211 with port 212, port 213 or port 214. The control device 220 is a three-way valve, having ports 221, 222 and 223, which permits selective interconnection of port 221 either with port 222 or port 223. The control device 230 is a reverse counting pneumatic impulse counter and valve, having ports 231, 232, 233 and 234, which permits either connection or disconnection of ports 231 and 232, which counts pneumatic impulses applied to port 234 and which is reset by a pneumatic impulse applied to port 233. The control device 240 is a spring-actuated valve, having ports 241, 242 and 243, which permits either connection or disconnection of ports 241 and 242, said connection occuring when pneumatic impulses are applied to port 243. The control device 250 is a pneumatically operated three-way valve, having ports 251, 252, 253, 254, 255 and 256, which permits the simultaneous interconnection of either port 256 with port 253 and port 254 with port 255, when pneumatic impulses are applied to port 252, or port 256 with port 254 and port 253 with port 255, when pneumatic impulses are applied to port 251, and which exhausts compressed air to the atmosphere through port 255. The control devices 261 and 262 are three-way automatic diverter valves each of which has a common port which is in selective communication with a normally closed port and a normally open port. The first limit valve 140 has an inlet port 141 and an exhaust port 142. The second limit valve 145 has an inlet port 147 and an exhaust port 146.

The compressed air source 200 is connected with port 211 of the multiport valve 210 by conduit or line (hereinafter referred to as line) 303. Port 213 of the multiport valve 210 is connected to port 221 of the three-way valve 220 by line 364. Port 212 of the multiport valve 210 is simultaneously connected with port 231 of the reverse counting pneumatic impulse counter and valve 230 by lines 304 and 305, with port 241 of the spring-actuated valve 240 by lines 304, 307 and 309, with inlet port 141 of the first limit valve 140 by lines 304, 307, 311 and 313 and with inlet port 147 of the second limit valve 145 by lines 304, 307, 311 and 315. Port 214 of the multiport valve 210 is connected with port 233 of the reverse counting pneumatic impulse counter and valve 230 by line 359. Port 223 of the three-way valve 220 is connected with the normally closed port of the three-way automatic diverter valve 262 by line 372. The common port of the three-way automatic valve 262 is connected with port 174 of the double-acting pneumatic cylinder 170 by line 337. The normally open port of the three-way automatic diverter valve 262 is connected with port 253 of the pneumatically operated three-way valve 250 by line 335. Port 222 of the three-way valve 220 is connected with the normally closed port of the three-way automatic diverter valve 261 by line 366. The common port of the three-way automatic diverter valve 261 is connected with port 173 of the double-acting pneumatic cylinder 170 by line 329. The normally open port of the three-way automatic diverter valve 261 is connected with port 254 of the pneumatically operated three-way valve 250 by line 327. Port 232 of the reverse counting pneumatic impulse counter and valve 230 is connected with port 243 of the spring-actuated valve 240 by line 321. Port 242 of the spring-actuated valve 240 is connected with port 256 of the pneumatically operated three-way valve 250 by line 323. The exhaust port 142 of the first limit valve 140 is connected with port 252 of the pneumatically operated three-way valve 250 by line 355. The exhaust port 146 of the second limit valve 145 is connected simultaneously with port 251 of the pneumatically operated three-way valve 250 by lines 343 and 347 and with port 234 of the reverse counting pneumatic impulse counter and valve 230 by lines 343 and 349.

Figure 4:
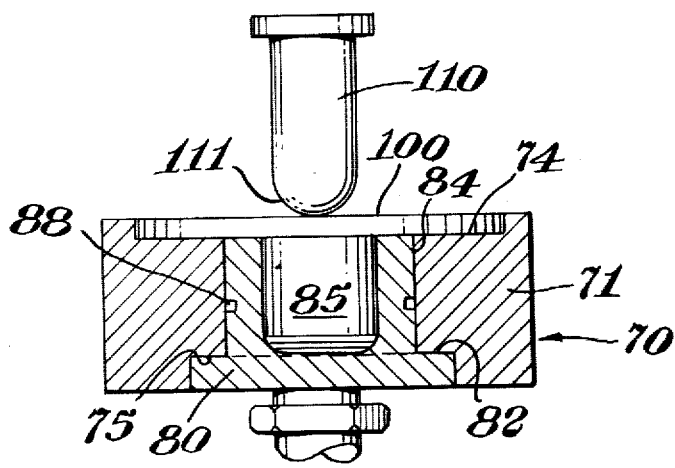
FIG. 4 is a schematic sectional view of a sample support means in accordance with the present invention.

In FIG. 4, there is schematically depicted a sectional view of the sample support means 70 in accordance with the present invention wherein the sample receiving means 71 is slidably fit onto the boss 84 of the ring pedestal 80, preferably secured in place by means of threadably engaging the set screw (not shown) with the internally screw-threaded aperture (not shown) of the sample receiving means 71 so as to cause the screw-threaded end of the set screw to project into the radially outwardly projecting groove 88 located on the boss 84 of the ring pedestal 80. The synthetic resinous product sample 100 is slidably fit into the recess 74 of the sample receiving means 71 and the impact member 110 is generally normal to the synthetic resinous product sample 100 with the first end 111 of the impact member 110 resting against that surface of the synthetic resinous product sample 100 which is proximate thereto. In this configuration, there is defined a support diameter which is equal in diameter to the diameter of the generally coaxial cavity 85 of the ring pedestal 80. The support diameter may be varied by a number of techniques, including but not limited to, placing a spacing element or spacing ring (not shown) between the first surface 82 of the ring pedestal 80 and the recess 75 of the sample receiving means 71, and reversing the sample receiving means 71 so that the recess 74, rather than the recess 75, is proximate to the first surface 82 of the ring pedestal 80.

Figure 5:
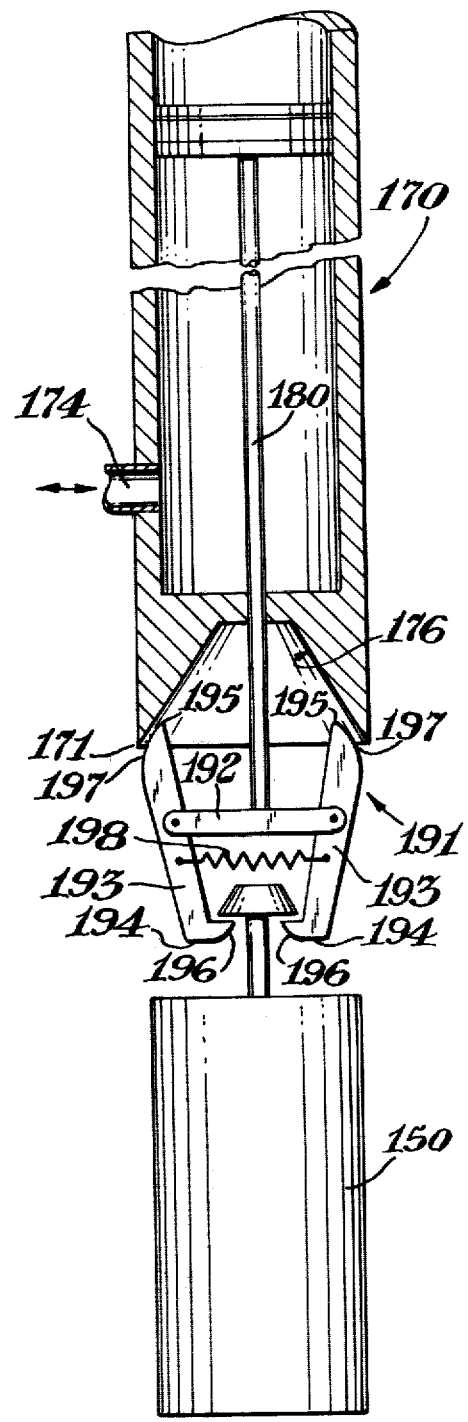
FIG. 5 is a schematic sectional view of a portion of an apparatus in accordance with the present invention for grasping and releasing an impact weight.

In FIG. 5, there is schematically depicted a cutaway sectional view of the double-acting pneumatic cylinder 170, a jaw assembly 191, and the impact hammer 150. The first end 171 of the double-acting pneumatic cylinder 170 defines a conical camming surface 176. The jaw assembly 191 comprises the piston rod 180, a central pivot bar 192, two jaws 193 and a tension spring 198. The jaws 193 have first ends 194 and second ends 195. As assembled the first ends 194 are remote from the first end 171 of the double-acting pneumatic cylinder 170 and terminate in opposed inwardly facing camming surfaces 196 which are inwardly convergent toward the piston rod 181, the second ends 195 are remote from the impact hammer 150 and terminate in opposed outwardly facing camming surfaces 197 which are outwardly divergent from the impact hammer 150, and the tension spring 198 is attached to the jaws 193 remote from the second ends 195 of the jaws 193 and from the central pivot bar 192, so as to resiliently tension the first ends 194 of the jaws 193 together. The jaw assembly 191 is one variation of the means 190 depicted in FIG. 1.

Figure 6:
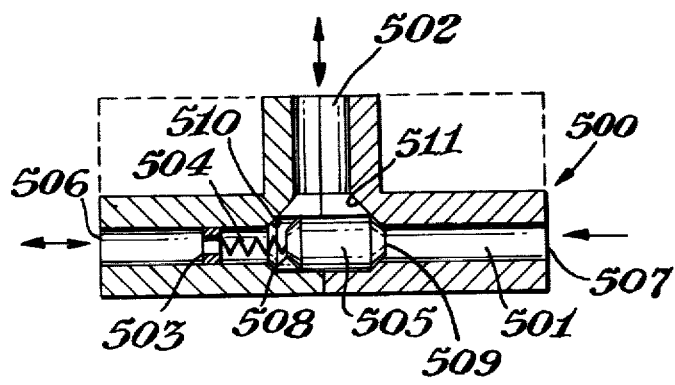
FIGS. 6 and 7 are schematic sectional views of an automatic diverter valve in accordance with the present invention.
Figure 7:
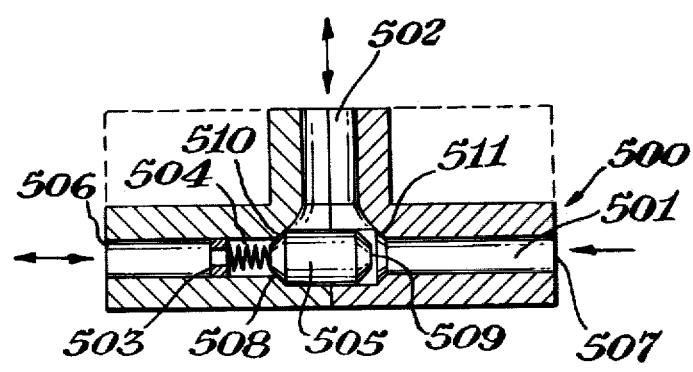

In FIGS. 6 and 7 there are schematically depicted sectional views of a three-way automatic diverter valve 500 which comprises a passage 501, an intersecting passage 502, a retaining ring 503, a compression spring 504 and a valving member 505. The passage 501 has a first end 506 and a second end 507. The valving member 505 has a first end 508 and a second end 509, each of which terminates in a seat engaging surface. Proximate to the intersection of passage 501 with passage 502 are the valve seats 510 and 511, the valve seat 510 being remote from the second end 507 of the passage 501 and the valve seat 511 being remote from the first end 506 of the passage 501. As assembled, the retaining ring 503 is affixed within the passage 501 proximate to the first end 506 and remote from the second end 507, the compression spring 504 has one end affixed to the first end 508 of the valving member 505 and one end resting against the retaining ring 503, and the valving member 505 is positioned so that the seat engaging surface of the second end 509 is engaged with the valve seat 511 (see FIG. 6). When a motive fluid under pressure, such as lubricated compressed air, enters the three-way automatic diverter valve 500 from the second end 507 of the passage 501, the compressed air causes the second end 509 of the valving member 505 to disengage from the valve seat 511 thereby compressing the compression spring 504 and causes the first end 508 of the valving member 505 to engage with the valve seat 510 thereby diverting the compressed air into the intersecting passage 502 (see FIG. 7). When the compressed air ceases to flow, the compression spring 504 acts on the first end 508 of the valving member 505 forcing the valving member 505 to disengage from the valve seat 510 and to engage with the valve seat 511 as in FIG. 6. The three-way automatic diverter valve 500 is the same as the three-way automatic diverter valves 261 and 262 depicted in FIG. 3.

Motive fluid under pressure, such as lubricated compressed air, flows from the source 200 through the line 303 to port 211 of the multiport valve 210. When the port 211 is selectively connected to port 212 of the multiport 210; compressed air flows from the port 212 simultaneously as follows: (a) via lines 304 and 305 to port 231 of the reverse counting pneumatic impulse counter and valve 230; (b) via lines 304, 307 and 309 to port 241 of the spring-actuated valve 240; (c) via lines 304, 307, 311 and 313 to inlet port 141 of the first limit valve 140; and (d) via lines 304, 307, 311 and 315 to inlet port 147 of the second limit valve 145. When ports 231 and 232 of the pneumatic impulse counter and valve 230 are connected, compressed air will flow from port 232 via line 321 to port 243 of the spring-actuated valve 240 thereby actuating the valve so as to interconnect ports 241 and 242 of the spring-actuated valve 240. When ports 241 and 242 of the valve 240 are interconncected, compressed air will flow from port 242 of the spring-actuated valve 240 via line 323 to port 256 of the pneumatically operated, three-way valve 250 which selectively connects port 256 with either port 253 or port 254 while simultaneously connecting the remaining port (either port 253 or port 254) with port 255 which is vented to the atmosphere. When port 256 is selectively connected with port 254 of the pneumatically operated, three-way valve 250, compressed air will flow from port 254 via line 327 into the normally open port and out of the common port of the three-way automatic diverter valve 261 via line 329 to port 173 which is located at the second end 172 of the double-acting pneumatic cylinder 170. The compressed air which flows through port 173 acts upon the piston (not shown) within the double-acting pneumatic cylinder 170 thereby causing the piston to move generally away from the second end 172 of the double-acting pneumatic cylinder 170. When the piston moves away from the second end 172, compressed air, which occupies the space between the piston and the first end 171, will flow from port 174 of double-acting pneumatic cylinder 170 via line 337, into the common port and out of the normally open port of the three-way automatic diverter valve 262 via line 335 to port 253 of the pneumatically operated, three-way valve 250, said port 253 being connected to port 255, the compressed air is then vented to the atmosphere. When ports 256 and 253 of the pneumatically operated, three-way valve 250 are connected, compressed air will flow in the opposite direction thereby causing the piston (not shown) to move generally toward the second end 172 of the double-acting pneumatic cylinder 170. The compressed air which occupies the space between the piston and the second end 172 is vented to the atmosphere via the interconnection of ports 254 and 255 of the pneumatically operated, three-way valve 250. Concurrent with the movement of the piston (not shown) within the double-acting pneumatic cylinder 170 is the actuation of either the first limit valve 140 or the second limit valve 145 but not both simultaneously. When the first limit valve 140 is actuated, the inlet port 141 and the exhaust port 142 are interconnected and the compressed air which enters the first limit valve 140 through the inlet port 141 will exit through the exhaust port 142 and will flow via line 355 to port 252 of the pneumatically operated, three-way valve 250. The compressed air which enters port 252 causes the pneumatically operated, three-way valve 250 to selectively interconnect ports 256 and 253 of the pneumatically operated, three-way valve 250 while simultaneously connecting ports 254 and 255 of the pneumatically operated, three-way valve 250. When the second limit valve 145 is actuated, the exhaust port 146 and the inlet port 147 are interconnected and the compressed air which enters the second limit valve 145 through the inlet port 147 will exit through the exhaust port 146 and will flow simultaneously to port 251 of the pneumatically operated, three-way valve 250 via lines 343 and 347 and to port 234 of the reverse counting pneumatic impulse counter and valve 230 via line 343 and 349. The compressed air which enters port 251 of the pneumatically operated, three-way valve 250 causes the pneumatically operated, three-way valve 250 to selectively interconnect ports 256 and 254 while simultaneously connecting ports 253 and 255 of the pneumatically operated, three-way valve 250. The compressed air which enters port 234 of the reverse counting pneumatic impulse counter and valve 230 causes the counter to rotate by one digit thereby diminishing the set number by one unit. When the set number reaches zero, ports 231 and 232 of the reverse counting pneumatic impulse counter and valve 230 are disconnected which, in turn, stops the flow of compressed air from port 232 of the reverse counting pneumatic impulse counter and valve 230 via line 321 to port 243 of the spring-actuated valve 240. When compressed air stops flowing to port 243 of the spring-actuated valve 240, the spring-actuated valve 240 operates to disconnect ports 241 and 242 of the spring-actuated valve 240 which thus halts the flow to compressed air to the pneumatically operated, three-way valve 250 and thereafter to the double-acting pneumatic cylinder 170.

When ports 211 and 214 of the multiport valve 210 are connected, compressed air will flow from port 214 of the multiport valve 210 via line 359 to port 233 of the reverse counting pneumatic impulse counter and valve 230. The compressed air which enters port 233 of the reverse counting pneumatic impulse counter and valve 230 causes the counter to return to the last number which has been set on the counter by an operator.

When ports 211 and 213 of the multiport valve 210 are connected, compressed air will flow from port 213 of the multiport valve 210 via line 364 to port 221 of the three-way valve 220. When port 221 is selectively connected with port 222 of the three-way valve 220, compressed air will flow from port 222 of the three-way valve 220 via line 366 into the normally closed port and out of the common port of the three-way automatic diverter valve 261 via line 329 to port 173 which is located at the second end 172 of the double-acting pneumatic cylinder 170. The compressed air which enters port 173 of the double-acting pneumatic cylinder 170 causes the piston (not shown) to move generally away from the second end 172 of the double-acting pneumatic cylinder 170. The compressed air which occupies the space between the piston and the first end 171 of the double-acting pneumatic cylinder 170 flows from port 174 of the double-acting pneumatic cylinder 170 via line 337 into the common port and out of the normally open port of the three-way automatic diverter valve 262 to port 253 of the pneumatically operated, three-way valve 250 which has been selectively connected to port 255 of the pneumatically operated, three-way valve 250 from which the compressed air will vent to the atmoshpere. When ports 221 and 223 of the three-way valve 220 are connected, compressed air will flow from port 223 of the three-way valve 220 via line 372 into the normally closed port and out of the common port of the three-way automatic diverter valve 262 via line 337 to port 174 which is located proximate to the first end 171 of the double-acting pneumatic cylinder 170. The compressed air which enters port 174 causes the piston (not shown) to move generally toward the second end 172 thereby causing the compressed air which occupies the space between the piston and the second end 172 of the double-acting pneumatic cylinder 170 to flow from port 173 of the double-acting pneumatic cylinder 170 via line 329 into the common port and out of the normally open port of the three-way automatic diverter valve 261 via line 327 to port 254 of the pneumatically operated, three-way valve 250 which has been selectively connected to port 255 from which the compressed air will vent to the atmosphere.

The control assembly 160, has two modes of operation, manual and automatic. When manual operation is desired, ports 211 and 213 of the multiport valve 210 are selectively connected and compressed air will flow as detailed above, when further selective connections are made between port 221 and either port 222 or port 223 of the three-way valve 220 and, respectively, between port 255 and either port 253 or port 254 of the pneumatically operated, three-way valve 250 so as to cause the piston (not shown) to move respectively toward or away from the second end 172 of the double-acting pneumatic cylinder 170. When automatic operation is desired, ports 211 and 212 of the multiport valve 210 are selectively connected and compressed air will flow, as detailed above, so as to cause the piston (not shown) to move repeatedly toward and away from the second end 172 of the double-acting pneumatic cylinder 170 provided that a number is preset on the reverse counting pneumatic impulse counter and valve 230. Automatic operation will cease when the digital number which is set on the reverse counting pneumatic impulse counter and valve 230 reaches zero. When an operator desires to repeat the number of impacts previously preset, ports 211 and 214 of the multiport valve 210 are selectively connected and compressed air will flow, as detailed above, so as to cause the impulse counter to be set at the last preset number.

The impact testing apparatus 10 is preferably vertically oriented so that the piston rod 180 moves generally up and down. In the preferred automatic mode of operation, the operator will set a selected number of cycles on the reverse counting pneumatic impulse counter and valve 230 and place the control assembly 160 in the automatic mode. The compressed air flow within the control assembly 160 causes the piston rod 180 to move repeatedly down, thereby causing the jaw assembly 191 to grasp the headed projection 153 of the impact hammer 150, and up, thereby raising the impact hammer 150 until the conical camming surface 176 of the double-acting pneumatic cylinder 170 actuates the jaw assembly 191 thus releasing the headed projection 153 of the impact hammer 150, said impact hammer 150 then falling within the hollow right circular cylinder 130 until the first end 151 of the impact hammer 150 impacts with the second terminal end 112 of the impact member 110 thereby transferring an impact energy through the impact member 110 to the synthetic resinous product sample 100 which is peripherally supported by the sample support means 70.

By way of further illustration, two high impact polystyrene compositions are evaluated for impact resistance employing an apparatus generally as depicted in FIGS. 1 and 2 using the automatic mode of operation. The samples are in the shape of discs 2½ inches in diameter and ⅛ inch thick. The samples were prepared at a melt temperature of 200° C. on a 4½ ounce injection molding machine manufactured by Toshiba Machine Company, Ltd. Three samples of each resin were tested at each of the heights listed in Table I below. Sample points of failure were found to lie within the last ten impacts as indicated opposite the drop heights in Table I below.

It has been found that micro-cracks usually occur on one side of the specimen when the cavity formed on the opposing side by the impact member is deep. For example, this can happen with a material of high elongation tested under a relatively high impact energy level. The micro-cracks, which result, are caused by rupturing the highly stretched outer surface of the product sample, and do not truly represent the failure of the product sample being tested. A more accurate representation of sample failure, for resins of the type tested, occurs when a crack penetrates through the sample without the prior formation of micro-cracks on the surface of the sample.

The energy level readings reported in Table I below are illustrative of the present invention. The different energy level readings for Impact Polystyrene A and Impact Polystyrene B demonstrate that similar Izod Impact Values yield very different practical toughness valves.

TABLE I

MULTI-IMPACT TEST AT DIFFERENT HEIGHTS
CONSTANT IMPACT ENERGY LEVEL

| | Impact Polystyrene A | Impact Polystyrene B |
|---|---|---|
| Izod Impact-foot-pounds/-inches | 1.38 | 1.34 |
| Falling Weight Impact-foot-pounds, 50% Failure | 2.9 | 5.4 |
| % Gel | 22.72 | 25.24 |
| Energy Level-0.67 foot-pound, Drop Height | | |
| 6 inches | 100–110 | 350–360 |
| 9 inches | 90–100 | 350–360 |

TABLE I-continued

MULTI-IMPACT TEST AT DIFFERENT HEIGHTS
CONSTANT IMPACT ENERGY LEVEL

| | Impact Polystyrene A | Impact Polystyrene B |
|---|---|---|
| 12 inches | 60–70 | 280–290 |

Although sample failure may be defined differently in each case, the principle of the present invention is readily applied to the testing of a wide variety of synthetic resinous materials.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. An improved impact testing apparatus of the type used for the evaluation of synthetic resinous products or test pieces in which a support means serves as a base in cooperative combination with a peripherally supporting sample support means, a slidably supported sample impacting means which is oriented generally normal to the sample support means, and a means for varying the height to which the sample impacting means is raised and dropped thereby imparting an impact energy to an impact region of a test piece, said impact region being a generally central unsupported surface portion of the test piece, and repeatedly imparting the impact energy until failure of the test piece occurs, wherein the sample support means is a ring pedestal which is connected to the support means and a peripherally supporting reversible sample receiving means having a first end and an opposing second end, the peripherally supporting reversible sample receiving means being supported by the ring pedestal so as to define a first support diameter when the first end of the peripherally supporting reversible sample receiving means is remote from the ring pedestal and a second support diameter when the second end of the peripherally supporting reversible sample receiving means is remote from the ring pedestal.

2. The apparatus according to claim 1 wherein additional support diameters are obtained by separating the ring pedestal and the peripherally supporting reversible sample receiving means by at least one spacing element.

3. The apparatus according to claim 1 wherein the ring pedestal has a first end which is attached to the support means and a second end which defines a cylindrical cavity which faces the impacting means.

4. The apparatus according to claim 1 wherein the peripherally supporting reversible sample receiving means has a first end, a second end and a partially cylindrical body, said body of the peripherally supporting reversible sample receiving means defining a peripheral boss or ridge at both the first end and the second end with the boss or ridge at the second end being of greater height and thickness than the boss or ridge at the first end; each boss extending parallel to the longitudinal axis of the ring pedestal.

5. The apparatus according to claim 4 wherein a sample restraint means is added.

6. The apparatus according to claim 5 wherein the sample restraint means is a combination of the peripheral boss or ridge which is located on the first and second ends of the peripherally supporting reversible sample receiving means and a generally planar annular plate which defines an opening, said opening having a diameter which is about equal to the diameter of the peripheral boss, and being coaxial with the longitudinal axis of the peripherally supporting reversible sample receiving means, the annular plate having a planar surface proximate to the peripherally supporting reversible sample receiving means, said planar surface having a surface area, the annular plate having a spaced relationship to the peripheral boss and being in a plane generally normal to the longitudinal axis of the sample receiving means.

7. The apparatus according to claim 6 wherein a material having a high coefficient friction is affixed to the surface area of the planar surface of the annular plate.

8. An improved impact testing apparatus of the type used for the evaluation of synthetic resinous products or test pieces in which a support means serves as a base in cooperative combination with a peripherally supporting sample support means, a slidably supported sample impacting means which is oriented generally normal to the sample support means, and a means for varying the height to which the sample impacting means is raised and dropped thereby imparting an impact force to an impact region of a test piece, said impact region being a generally central unsupported surface portion of the test piece, and continuing to impart the impact force until failure of the test piece occurs, wherein the improvement comprises:

(a) a sample impacting means having two pieces, an impact member which has a first end, a second end and a generally solid rotationally symmetrical body, the first end generally defining a hemispherical shape and the second end generally defining a radially outward projecting flange, the member being oriented so that the axis of generation of the body is generally centrally disposed with respect to the sample receiving means, and the first end being proximate to, rather than remote from, the impact region of the product sample, and an impact hammer which has a generally solid right cylindrical body, a first end and a second end, the first end terminating in a generally planar surface, the second end terminating in a headed projection, said headed projection having camming surfaces outwardly divergent toward the body of the impact hammer, and the hammer being slidably supported by the support means and oriented so that the longitudinal axis of the hammer is generally coaxial with the axis of generation of the impact member and so that the second end is remote from the impact member, the impact force being imparted to the impact region when the first end of the impact hammer strikes the second end of the impact member, the impact force being of a magnitude such that there is substantially no rebounding of the first end of the impact member away from the impact region after the impact force is imparted;

(b) a sample support means which is a combination of two pieces, a ring pedestal which supports a peripherally supporting reversible sample receiving means, the ring pedestal having a first end which is attached to the support means and a second end which defines a cylindrical cavity which faces the second end of the impact member and the peripherally supporting reversible sample receiving means having a first end, a second end and a partially cylindrical body, said partially cylindrical body defining a peripheral boss or ridge at both the first end and the second end with the boss or ridge at the second end being of greater height and thickness than the boss or ridge at the first end, each boss extending parallel to the longitudinal axis of the ring pedestal, the combination of the ring pedestal and the peripherally supporting reversible sample receiving means thereby providing more than one support diameter;

(c) a means adapted to provide repetition which comprises in cooperative combination: (i) a double-acting pneumatic cylinder which is oriented generally normal to the impact region so that the motion of a piston which is within the cylinder is generally up and down, alternately toward and away from the impact region, said cylinder being affixed to the support means; (ii) the piston rod which has a first end attached to the piston and a second end which is remote from the piston; (iii) a resiliently tensioned cam-actuated jaw assembly adapted to grasp and release the second end of the impact hammer, the jaw assembly being attached to the second end of the piston rod; and (iv) a reverse counting pneumatic impulse counting control apparatus which is connected to the double-acting pneumatic cylinder and which controls the operation thereof, the control apparatus comprising, in cooperative combination, a source of motive fluid such as lubricated compressed air, a reverse counting pneumatic impulse counter and valve, a valving means whereby the direction of flow of the motive fluid may be repeatedly changed, and a network of interconnecting conduits or lines which interconnect the valving means, the source of motive fluid, the reverse counting pneumatic impulse counter and valve and the double-acting pneumatic cylinder to thereby cause the piston within the double-acting pneumatic cylinder to move to and fro; and (d) a sample restraint means which is a combination of the peripheral boss or ridge which is located on the first and second ends of the peripherally supporting reversible sample receiving means and a generally planar annular plate which defines an opening, said opening having a diameter which is about equal to the diameter of the peripheral boss, and being coaxial with the longitudinal axis of the peripherally supporting reversible sample receiving means, the annular plate having a planar surface proximate to the peripherally supporting reversible sample receiving means, said planar surface having a surface area, the annular plate having a spaced relationship to the peripheral boss and being in a plane generally normal to the longitudinal axis of the peripherally supporting reversible sample receiving means, and the surface area of planar surface of the annular plate having affixed thereto a material having a high coefficient of friction.

* * * * *